(12) United States Patent
Sarlak et al.

(10) Patent No.: US 9,566,564 B2
(45) Date of Patent: Feb. 14, 2017

(54) METHODOLOGY FOR THE FORMATION OF AN EXTRACTIVE AGENT OF POLYMERIZED CARBON NANOTUBES ENCAPSULATING PHENOL NANOPARTICLES USED FOR DNA EXTRACTION AND PURIFICATION, AND PRODUCT THEREOF

(71) Applicants: Nahid Sarlak, Tehran (IR); Sayyed Mostafa Jafari, Kashan (IR)

(72) Inventors: Nahid Sarlak, Tehran (IR); Sayyed Mostafa Jafari, Kashan (IR)

( * ) Notice: Subject to any disclaimer, the term of this patent is extended or adjusted under 35 U.S.C. 154(b) by 183 days.

(21) Appl. No.: 14/615,398

(22) Filed: Feb. 5, 2015

(65) Prior Publication Data

US 2015/0224475 A1 Aug. 13, 2015

Related U.S. Application Data

(60) Provisional application No. 61/936,874, filed on Feb. 7, 2014.

(51) Int. Cl.
| | | |
|---|---|---|
| *C01B 31/02* | (2006.01) | |
| *B01J 20/32* | (2006.01) | |
| *B01J 20/26* | (2006.01) | |
| *B01J 20/22* | (2006.01) | |
| *C07C 39/04* | (2006.01) | |
| *B01J 20/20* | (2006.01) | |

(52) U.S. Cl.
CPC ......... *B01J 20/3278* (2013.01); *B01J 20/205* (2013.01); *B01J 20/22* (2013.01); *B01J 20/265* (2013.01); *C01B 31/0273* (2013.01); *C07C 39/04* (2013.01); *Y10S 977/746* (2013.01)

(58) Field of Classification Search
None
See application file for complete search history.

(56) References Cited

U.S. PATENT DOCUMENTS 8,460,711 B2 * 6/2013 Atyabi ................ A61K 9/0092
424/490

OTHER PUBLICATIONS

Adeli et al., "Encapsulation of Palladium Nanoparticles by Multiwall Carbon Nanotubes-graft-Poly(citric acid) Hybrid Materials" Journal of Applied Polymer Science (2010) vol. 116, pp. 2188-2196.*

* cited by examiner

*Primary Examiner* — Eric Olson
(74) *Attorney, Agent, or Firm* — NovoTechIP International PLLC (57) ABSTRACT

A method for synthesis of nanocomposites using polymerized carbon nanotubes and phenolic compounds, such as 2,4-dichlorophenol, 4-nitrophenol, 2-nitrophenol, 4-chlorophenol, 2,4,6-trinitrophenol and phenol, in aqueous media, as well as the application of one of such nanocomposites, namely MWCNT-g-PCA-Phenol, as a DNA extraction agent. The aforementioned nanocomposites enable the isolation of genomic DNA of plant samples. Pursuant to the present invention, the toxicity of free phenols used in DNA extraction is decreased since very low concentrations of phenol are required in the method, as compared to conventional techniques which employ saturated phenol solutions. This remarkable advantage is due to the encapsulation of the phenol nanoparticles into the polymerized carbon nanotubes.

20 Claims, 12 Drawing Sheets

METHODOLOGY FOR THE FORMATION OF AN EXTRACTIVE AGENT OF POLYMERIZED CARBON NANOTUBES ENCAPSULATING PHENOL NANOPARTICLES USED FOR DNA EXTRACTION AND PURIFICATION, AND PRODUCT THEREOF

CROSS REFERENCE TO RELATED APPLICATION

The present invention claims priority from pending U.S. Provisional Patent Application Ser. No. 61/936,874, filed Feb. 7, 2014, entitled "Extractive agent of polymerized carbon nanotubes encapsulating phenol nanoparticles for DNA extraction and purification," the subject matter of which is incorporated by reference herein in its entirety.

SPONSORSHIP STATEMENT

This application has been sponsored by the Iranian Nanotechnology Initiative Council, which does not have any rights in this application.

TECHNICAL FIELD

The present invention generally relates to extractive agents, and more particularly relates to extractive agent of polymerized carbon nanotubes encapsulating phenol nanoparticles for DNA extraction and purification.

BACKGROUND OF THE INVENTION

The initial step in many molecular biology procedures involves the analytical separation of DNA fragments. As is known to those skilled in the art, general steps of nucleic acid purification include cell lysis, which disrupts the cellular structure to create a lysate; inactivation of cellular nucleases, such as deoxyribonuclease (DNase) and Ribonuclease (RNase); and separation of desired nucleic acids from cell debris.

As is understood in the art, a mixture of phenol:chloroform:isoamyl alcohol (about 25:24:1) is used for denaturing proteins, and inhibiting the aforesaid RNase activity. Proteins, lipids, carbohydrates and cell debris are removed through extraction of the aqueous phase with the organic mixture of phenol and chloroform. A biphasic emulsion is formed when phenol and chloroform are added. By centrifugation of the aforementioned emulsion, the hydrophobic layer settled at the bottom and the hydrophilic layer on top. The upper phase, which contains DNA, is collected, and the DNA could be precipitated from the supernatant by adding ethanol or isopropanol in 2:1 or 1:1 ratios and high concentrations of salt. Then, the DNA precipitate is collected by centrifugation, and the salt is rinsed with ethanol.

The DNA pellet is then dissolved within a Tris-Ethylenediaminetetraacetic (TE) buffer or sterile distilled water, where Ethylenediaminetetraacetic is also termed EDTA.

For plant extraction, grinding the sample after freezing it in liquid nitrogen is necessary to break down cell wall material of the sample and allow accessing the nucleic acid, while harmful cellular enzymes and biochemicals remain inactivated. After grinding the sample, it can be re-suspended in a suitable buffer, such as cetyltrimethylammonium bromide (CTAB) or sodium dodecyl sulfate (SDS). This method also uses organic solvents and alcohol precipitation in later steps. Insoluble particles are removed through centrifugation to purify the nucleic acid. Soluble proteins and other materials are first mixed with chloroform, and then are separated by centrifugation. Nucleic acid must be precipitated after this from the supernatant, and washed thoroughly to remove contaminating salts. The purified nucleic acid is then resuspended, and stored in a TE (Tris-EDTA) buffer, preferably at $-20°$ C., or in sterile distilled water.

The conventional methods described hereinabove require repeated centrifugation steps, followed by removal of supernatants, depending on the type of specimen and additional mechanical treatments, which is time consuming.

As is known to a person skilled in the art, saturated solutions of phenol are used in the conventional methods of DNA extraction and purification described hereinabove. Phenol is a flammable, corrosive and toxic carbolic acid, and, therefore, using its saturated solution is unfavorable, as it is harmful to both humans and environment. Thus, phenol and substituted phenols have been included as priority pollutants in the list of the European Union (EU) and US Environmental Protection Agency (EPA).

There is, therefore, a present need for improved methodologies and techniques for the extraction and purification of DNA.

It is, therefore, an object of the present invention to provide an alternative extraction agent for DNA extraction and purification, which facilitates a faster and safer extraction process.

These and many other objects are met in various embodiments of the present invention, offering significant advantages over the known prior art.

SUMMARY OF THE INVENTION

A method for synthesizing an extractive agent for DNA extraction and purification is set forth. Carbon nanotubes are first oxidized. Next, the oxidized carbon nanotubes are mixed into monohydrated citric acid to synthesize carbon nanotubes grafted with poly(citric acid). The carbon nanotubes grafted with poly(citric acid) are then mixed with phenolic solutions to synthesize carbon nanotubes grafted with poly(citric acid) encapsulating phenol nanoparticles.

In some implementations, carbon nanotubes can be oxidized by mixing the carbon nanotubes with nitric acid and sulfuric acid in a first mixture. In some embodiments of the present invention, the ratio of nitric acid to the sulfuric acid in the first mixture is preferably about 1 to 3. The carbon nanotubes can be multi-walled carbon nanotubes. The oxidized carbon nanotubes can be extracted by drying the aforementioned oxidized carbon nanotubes in a heated environment.

In some embodiments of the present invention, phenolic solution can be aqueous solutions of phenol, 4-nitrophenol (4-NP), 4-chloro-3-methylphenol (4-CP), 2, 4-dichlorophenol (2,4-DP), 2,4,6-trinitrophenol (2,4,6-TNP), and mixtures thereof.

Details of one or more implementations and/or embodiments of the present invention are set forth in the accompanying DRAWINGS and the description below. Other aspects that can be implemented will be apparent from the description and the DRAWINGS, and from the claims.

BRIEF DESCRIPTION OF THE DRAWINGS

While the specification concludes with claims particularly pointing out and distinctly claiming the subject matter that is regarded as forming the present invention, it is believed that the invention will be better understood from the following description taken in conjunction with the accompanying DRAWINGS, where like reference numerals designate like structural and other elements, in which:

DETAILED DESCRIPTION OF THE INVENTION

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

It should be understood by a person skilled in the art that the invention described herein relates to the capability of multi-walled carbon nanotubes grafted with poly(citric acid) (hereinafter "MWCNT-g-PCA") for encapsulation of some phenols in aqueous media, wherein the trapping of phenols by MWCNT-g-PCA hybrid materials causes the encapsulation of phenols onto the surface of multi-walled carbon nanotubes (hereinafter MWCNTs).

In another aspect of the present invention, one of the resulting phenolic nanocomposites synthesized, as mentioned hereinabove, namely MWCNT-g-PCA-Phenol, is then applied for the phenolic purification of DNA.

As is known from the prior art, initially, MWCNTs, nitric acid (HNO3), and sulfuric acid (H2SO4) are mixed to oxidize the MWCNTs in a first mixture. MWCNTs generally have 3 to 15 walls, an outer diameter of 10 to 40 nanometers, a length of 1 to 10 micrometers, and a specific surface area of 40 to 300 $m^2/g$. In some implementations, the MWCNTs can be synthesized over nanoporous a catalyst, such as cobalt and molybdenum/magnesium oxide (CoMo/MgO), by a chemical vapor deposition method at a temperature of about 900° C.

The nitric acid and the sulfuric acid can be mixed at, for example, a 1:3 ratio. For instance, in some implementations, 2 g of MWCNTs can be mixed with 40 mL of a nitric and sulfuric acid solution including about 10 mL of nitric acid and about 30 mL of sulfuric acid to oxidize the MWCNTs in the first mixture.

The mixture of MWCNTs, nitric acid, and sulfuric acid can be mixed in a reaction flask and refluxed for about 24 hours at 120° C. Then the resultant first mixture can then be cooled, diluted with distilled water, and filtered. Afterward the filtered product could then be washed with distilled water.

Next, the oxidized MWCNTs are extracted from the first mixture. The filtrate resulting from can, for example, be dried in a vacuum oven for about 24 hours at 40° C. to extract the oxidized MWCNTs.

It should be understood that it is difficult to do phenol particle deposition onto the surface of MWCNTs while controlling the homogeneity of the aforementioned deposition by the conventional methods, since the surface of MWCNTs is rather neutral. It is known, however, to a person skilled in the art that oxygen-containing functional groups, such as —COOH and —OH, play an important role in anchoring metal nanoparticles onto the walls of MWCNTs.

Figure 1:
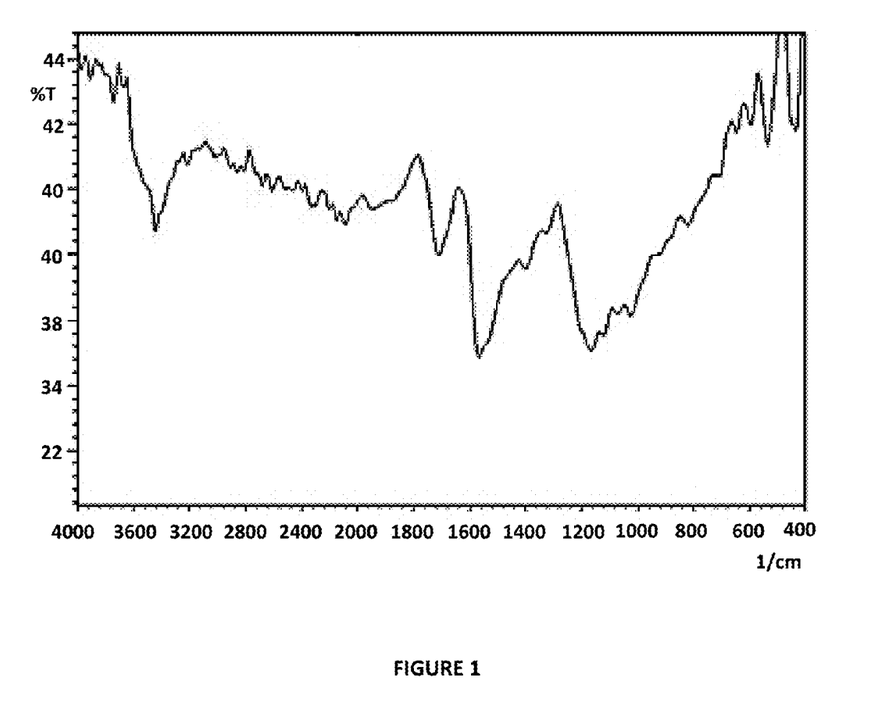
FIG. 1 illustrates a Fourier transform infrared spectrum of oxidized multi-walled carbon nanotubes.

With reference now to FIG. 1 of the DRAWINGS, this image shows the Fourier transform infrared spectrum of oxidized MWCNTs. As shown in the Figure, absorbance bands of hydroxyl functional groups, carbonyl groups and the carbon-to-carbon double bonds (hereinafter "C═C") appear at 3440, 1700 and 1590 and 1400 $cm^{-1}$, respectively. These surface functional groups provide active sites for the interaction with phenol molecules. Hence, the extent of phenol deposition on the surface of the carbon nanotubes depends on the density of the aforementioned surface functional groups.

Functionalized MWCNTs are then added to a polymerization ampoule equipped with a magnetic stirrer and a vacuum inlet. Monohydrate citric acid is also added to the ampoule and it is sealed under vacuum. Subsequently, the mixture is heated. Water, which is a byproduct of the reaction, is removed by the vacuum inlet, and the reaction temperature is raised, preferably to about 140° C. The polymerization continues under dynamic vacuum. The resulting mixture is then cooled and dissolved in tetrahydrofouran (THF). The final product, which is an MWCNT-g-PCA hybrid material, is then precipitated in cyclohexane. The purified MWCNT-g-PCA is obtained as a viscous coffee-brown compound.

In some embodiments of the instant invention, 0.05 grams of oxidized MWCNTs and 2.5 grams of monohydrated citric acid are added to a polymerization ampoule equipped with a magnetic stirrer and a vacuum inlet. The second mixture can be heated to about 120° C. and stirred for 30 minutes. Then, the temperature of the second mixture can be gradually increased to about 140° C. over a time period of about one hour, while a dynamic vacuum is operated at proper intervals to remove the water from the second mixture. Following the removal of water by the dynamic vacuum, the reaction temperature can be raised to about 160° C., and polymerization can continue at this temperature for about one and a half hours. The resulting product can then be cooled and dissolved in tetrahydrofouran.

In some embodiments, the MWCNT-g-PCA can be purified by precipitating the second mixture in cyclohexane to extract the free citric acid, leaving the purified MWCNTs-g-PCA in tetrahydrofouran (THF).

Figure 2:
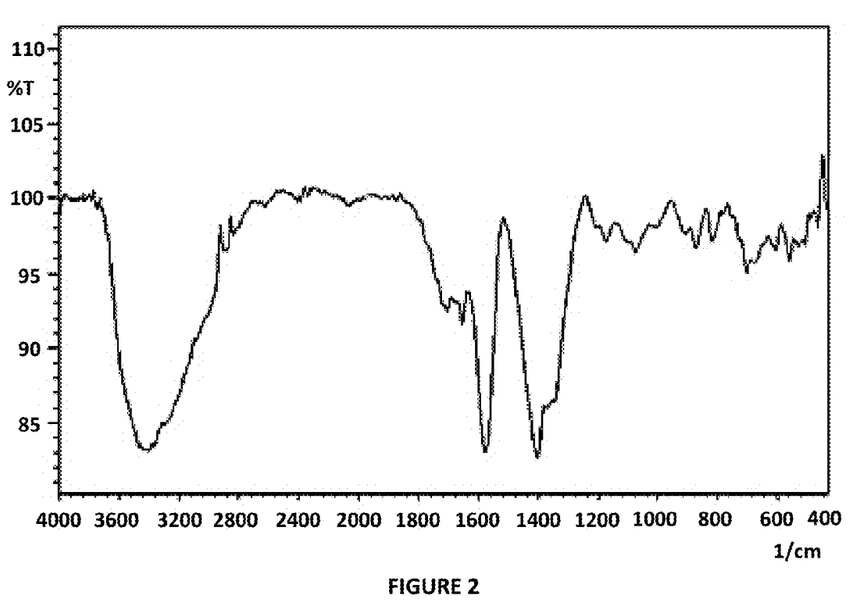
FIG. 2 illustrates a Fourier transform infrared spectrum of multi-walled carbon nanotubes grafted with poly(citric acid)

With reference now to FIG. 2 of the DRAWINGS, this image shows the Fourier transform infrared spectrum of MWCNT-g-PCA. As illustrated, a broad absorbance band at 3620-2700 $cm^{-1}$ can be identified for hydroxyl functional groups of the grafted poly(citric acid). In this spectrum, two absorbance bands of carbonyl groups of citric acid appear at 1730 and 1660 $cm^{-1}$. The absorbance band of C=C bonds of MWCNT appears at 1590 $cm^{-1}$.

Figure 3:
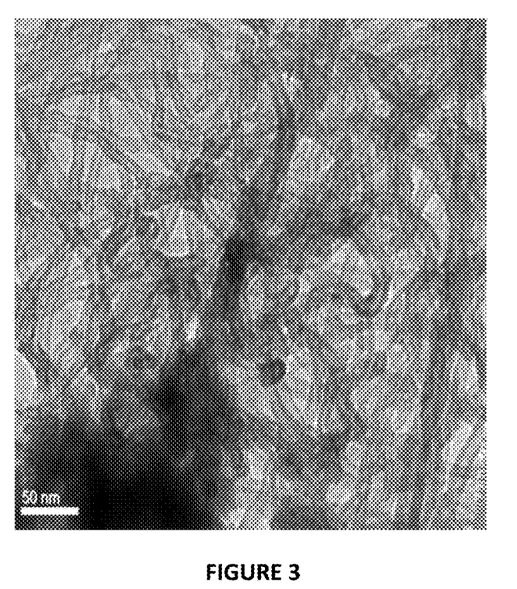
FIG. 3 shows a high-resolution, transmission electron microscope (HRTEM) image of the multi-walled carbon nanotubes grafted with poly(citric acid), such as demonstrated in FIG. 2, at 50 nm.
Figure 4:
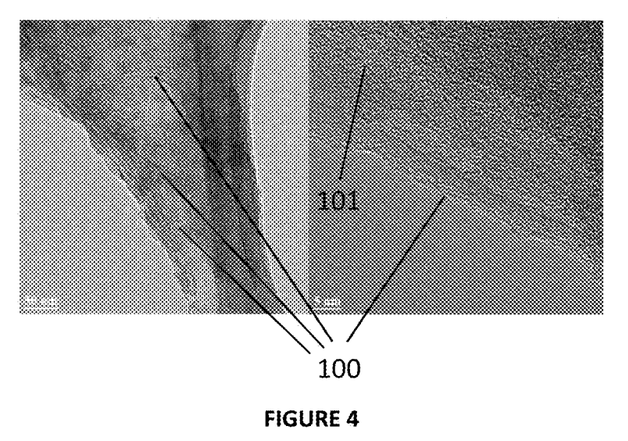
FIG. 4 are transmission electron microscope (TEM) images of the multi-walled carbon nanotubes grafted with poly(citric acid), at 50 nm (left) and 5 nm (right)
Figure 5A:
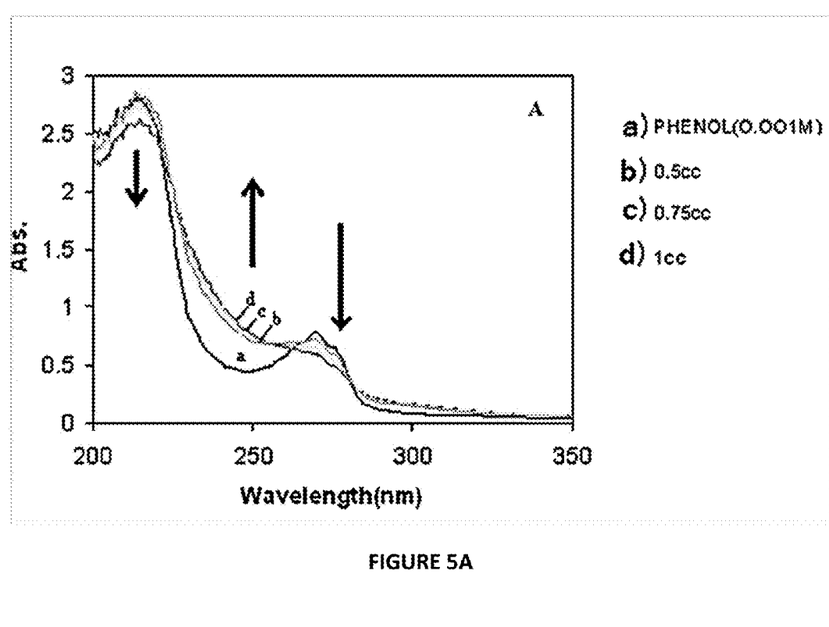
FIG. 5A illustrates titration diagrams and information regarding aqueous solutions of phenol.
Figure 5B:
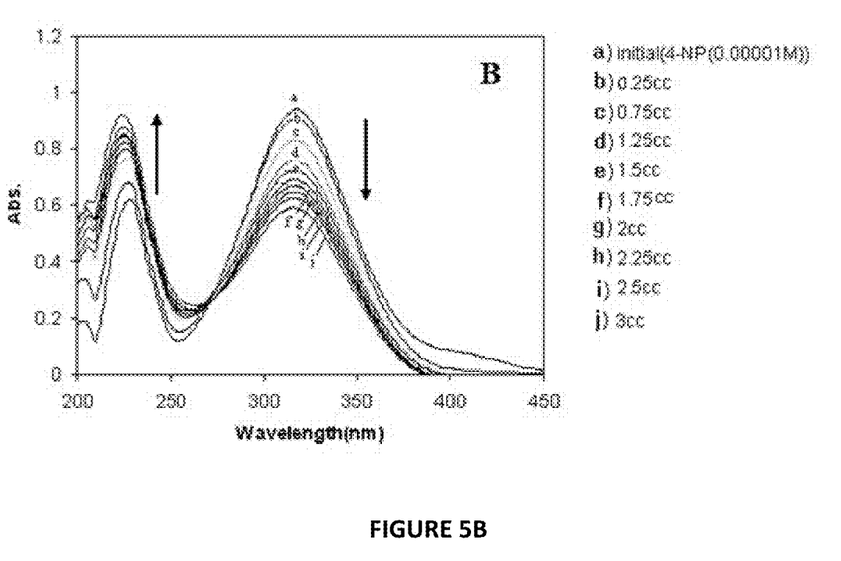
FIG. 5B illustrates titration diagrams and information regarding 4-nitrophenol (4-NP)
Figure 5C:
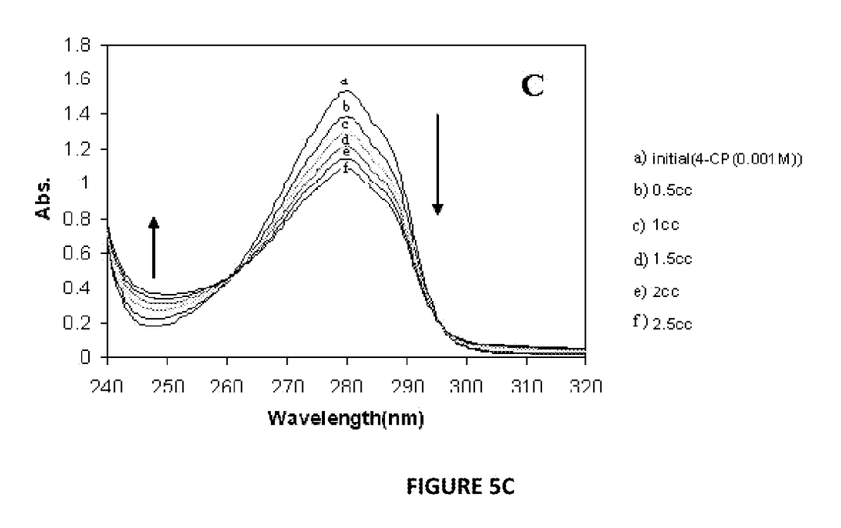
FIG. 5C illustrates titration diagrams and information regarding 4-chloro-3-methylphenol (4-CP)
Figure 5D:
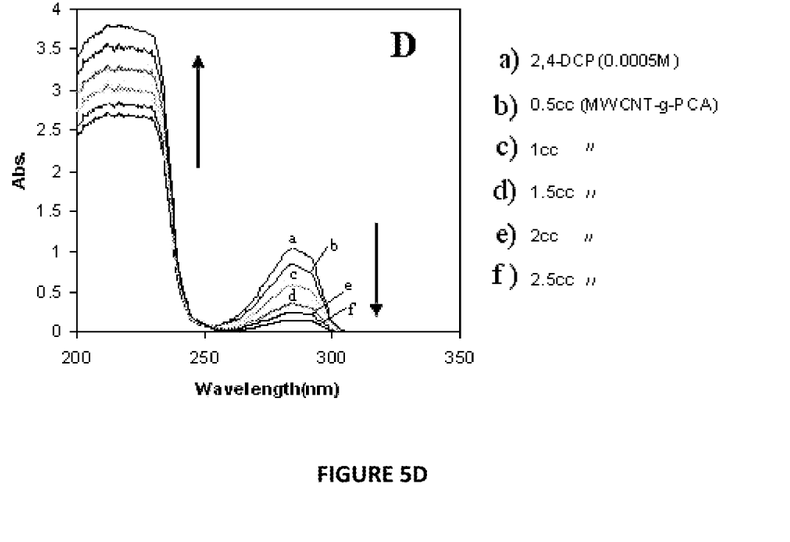
FIG. 5D illustrates titration diagrams and information regarding of 2,4-dichlorophenol (2,4-DP)
Figure 5E:
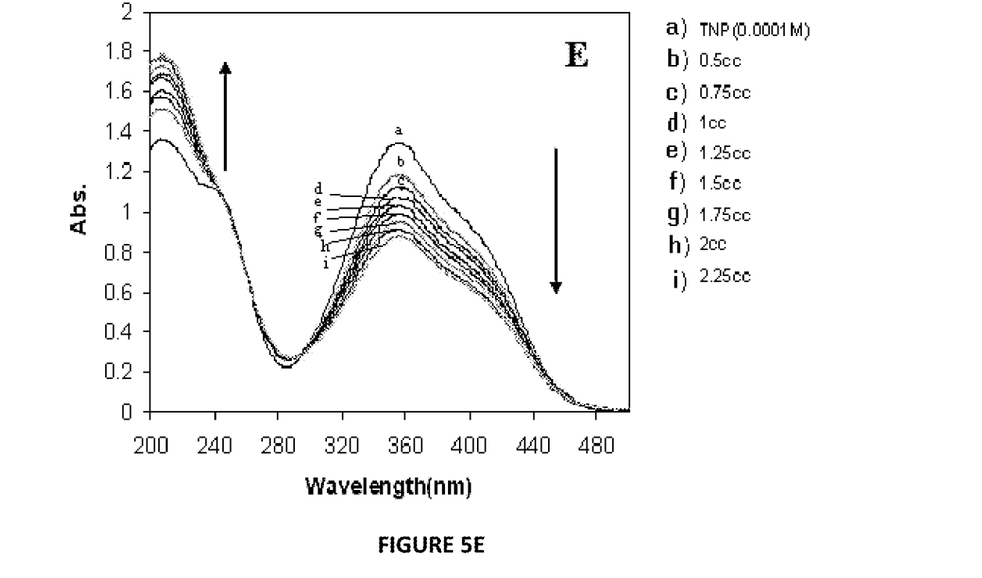
FIG. 5E illustrates titration diagrams and information regarding 2,4,6-trinitrophenol (2,4,6-TNP or TNP)
Figure 5F:
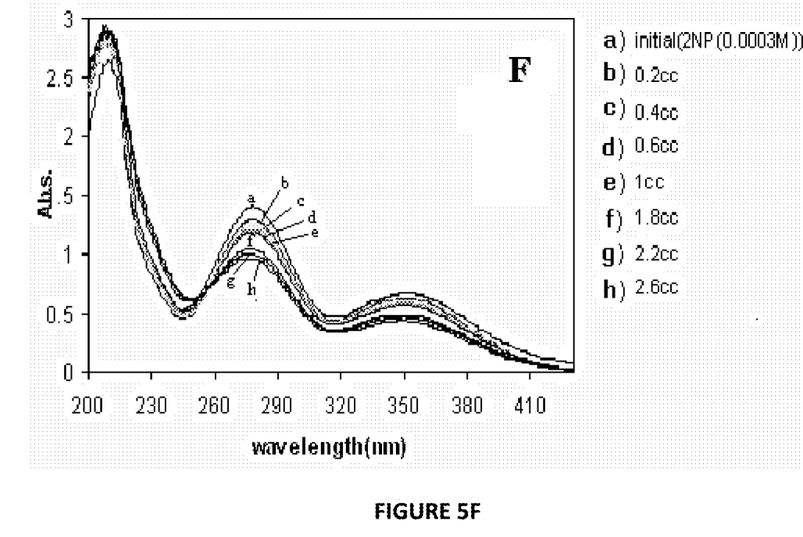
FIG. 5F illustrates titration diagrams and information regarding multi-walled carbon nanotubes grafted with poly (citric acid) (MWCNT-g-PCA)

With reference now to FIGS. 3 and 4 of the DRAWINGS, FIG. 3 illustrates a high-resolution transmission electron microscope (HRTEM) image of the aforesaid MWCNT-g-PCA solution; and FIG. 4 illustrates transmission electron microscope (TEM) views of the MWCNT-g-PCA solution at image resolutions of 50 nm (left) and 5 nm (right). As illustrated, MWCNTs 100 are held by a poly(citric acid) shell 101.

An aqueous solution of MWCNT-g-PCA and a phenolic solution are mixed in the presence of a phosphate buffer solution to synthesize MWCNT-g-PCA encapsulating phenol (hereinafter "MWCNT-g-PCA/Phenol"). The resulting solution is placed in an ultrasonic bath for the phenol molecules to be thoroughly dispersed within the polymeric shell of the hybrid materials. Then the solution is stirred at room temperature. The water can be removed from the mixture by a vacuum, and finally, the residue is dissolved in THF.

In alternate embodiments of the present invention, the phenolic solution mentioned hereinabove can be aqueous solutions of phenol, 4-nitrophenol (4-NP), 4-chloro-3-methylphenol (4-CP), 2,4-dichlorophenol (2,4-DP), or 2,4,6-trinitrophenol (2,4,6-TNP) or a mixture thereof.

With reference now to FIG. 5 of the DRAWINGS, there are illustrated therein graphic representations of the phenolic solutions titration by gradual addition of MWCNT-g-PCA fresh solutions. As is illustrated in FIGS. 5A-F, the intensity of the maximum wavelength of the phenolic solution in the presence of different concentrations of the MWCNT-g-PCA hybrid materials decreases. For example, when an aqueous solution of MWCNT-g-PCA is added to a 0.01 molar solution of phenol, the intensity of the absorption peak of phenol in 270 nm decreases, which shows a decrease in the concentration of free phenol and an increase in the concentration of the encapsulated phenol into the poly(citric acid) shell, as illustrated in connection with the information set forth in FIG. 5A. Indeed, during the titration of the phenolic solutions with the MWCNT-g-PCA solution, several isobestic points appear, implying the interaction between the phenolic solutions and the polymerized carbon nanotube solution. Similar results appear in FIGS. 5B-5F as well.

Figure 6:
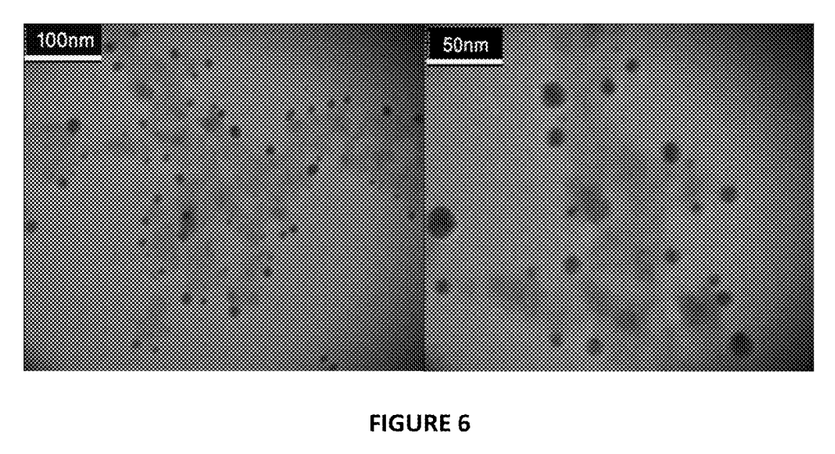
FIG. 6 are two transmission electron microscope (TEM) images of the aforementioned multi-walled carbon nanotubes grafted with poly(citric acid) encapsulating phenol before vacuum evaporation, with image resolutions of 100 nm (left) and 50 nm (right), which confirm the presence of phenol nanoparticles in the polymeric shell, pursuant to the teachings of the present invention.

With reference now to FIG. 6 of the DRAWINGS, there are shown transmission electron microscope (TEM) images of the aforementioned MWCNT-g-PCA/Phenol hybrid materials with image resolutions of 100 nm (left) and 50 nm (right). As above, these images indicate the presence and the distribution of phenol nanoparticles in the polymeric shells before vacuum evaporation.

Figure 7:
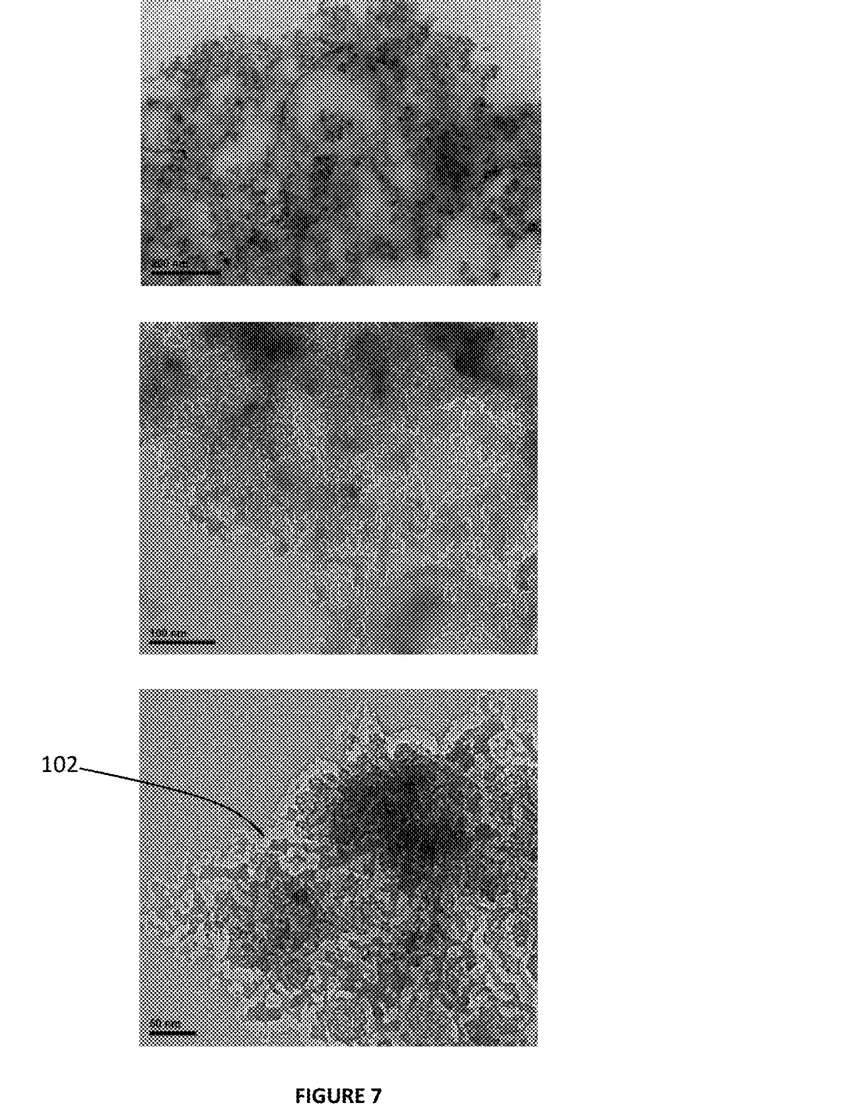
FIG. 7 are three transmission electron microscope (TEM) images of the multi-walled carbon nanotubes grafted with poly(citric acid) encapsulating phenol after vacuum evaporation, with image resolutions of 200 nm, 100 nm, and 50 nm, respectively, confirming the presence of phenol nanocrystals in the polymeric shell after vacuum evaporation, pursuant to further teachings of the present invention.

With reference now to FIG. 7 of the DRAWINGS, there are shown transmission electron microscope (TEM) images of the aforementioned MWCNT-g-PCA/Phenol hybrid materials at different image resolutions, particularly 200 nm, 100 nm, and 50 nm, respectively. These images likewise confirm the presence of phenol nanocrystals, designated by the reference numeral 102, in the polymeric shell after vacuum evaporation.

The aforementioned phenolic nanocomposites were employed, as a new extraction agent, to the extraction of genomic DNA.

In order to test the effectiveness of the aforementioned MWCNT-g-PCA/Phenol as a new extractive agent for DNA extraction and purification, plant samples were prepared in three growing stages (A: typical gone-up; B: sample adults; and C: young specimens), and the extraction process was carried out using MWCNT-g-PCA/Phenol as the extractive agent. Two replicates were performed on each sample. For comparison, a young plant was selected as a control sample and its DNA was extracted without using phenolic nanocomposites. A spectrophotometric method (Biophotometer) was used to determine the concentration and purity of the extracted DNA, as is common in the art, and to determination the quality of the extracted DNA an agarose gel method was used. An agarose gel method determines the concentration and purity of extracted DNA for a sample, which is diluted from 5 to 195.

The absorbance of DNA at 260 nm (maximum wavelength for DNA, Xmax) and the absorbance of protein at 280 nm (maximum wavelength for protein, Xmax) were determined by a biophotometer. Then, the ratio of the absorbance of DNA at 260 nm to the absorbance of protein at 280 nm was calculated. The resultant ratio shows the impurity of DNA. This ratio for a pure sample of DNA is 1.8-2. If this ratio is less than 1.8, the intensity of infection in protein to DNA is higher.

Considering that the concentration of double-stranded DNA at 260 nm and an optical density (hereinafter "OD") of 1 is 50 µg/ml, concentrations of the samples were calculated according to the following formula:

100(Dilution factor)×50 (µg/ml)×absorbance at 260 (nm)=DNA concentration (µg/ml).

The results in TABLE 1 presented herein bellow, indicate that the samples A, B, and C, which are extracted using the new phenolic nanocomposite, have higher OD values compared to the control sample K, which was extracted using phenol in a conventional method. In terms of performance (quantity and quality of DNA), high OD values for samples A, B, and C in comparison with the control sample K indicate high efficiency and low contamination in extracting plant genomic DNA. Numbers 1 and 2 indicate the replication or repetition of some of the tests for each sample.

TABLE 1

| Concentration | OD | Replicate | Sample |
| --- | --- | --- | --- |
| 641 ng/µl | 1.88 | 1 | A |
| 512 ng/µl | 1.7 | 2 | |
| 995 ng/µl | 1.9 | 1 | B |
| 765 ng/µl | 1.84 | 2 | |
| 812 ng/µl | 1.97 | 1 | C |
| 954 ng/µl | 1.95 | 2 | |
| 345 ng/µl | 1.34 | — | K |

A small amount of phenol solution (0.1 M) is used in the preparation of the aforementioned MWCNT-g-PCA/Phenol nanocomposite, and given the toxic nature of phenol, this is a considerable advantage over conventional methods, in which saturated solutions of phenol are used. Thus, simply using the proposed phenolic nanocomposite for DNA extraction from biological samples is more environmental-friendly.

In the present invention, phenol is encapsulated as nanoparticles. Accordingly, this increases the surface area, which leads to a more effective and faster DNA extraction process.

It is to be understood the implementations are not limited to the particular processes, devices, and/or apparatus described which may, of course, vary. It is also to be understood that the terminology used herein is for the purpose of describing particular embodiments only, and is not intended to be limiting. As used in this application, the singular forms "a", "an" and "the" include plural referents unless the content clearly 10 indicates otherwise.

Reference in the specification to "one embodiment" or "an embodiment" means that a particular feature, structure, characteristic, or function described in connection with the embodiment is included in at least one embodiment herein. The appearances of the phrase "in some embodiments" in the specification do not necessarily 15 all refer to the same embodiment. Accordingly, other embodiments and/or implementations are within the scope of this application.

While the present invention has been illustrated by the description of the embodiments thereof, and while the embodiments have been described in detail, it is not the intention of the Applicant to restrict or in any way limit the scope of the appended 20 claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departure from the breadth or scope of the applicant's concept. Furthermore, although the present invention has been described in connection with a number of exemplary embodiments and implementations, the present invention is not so limited but rather covers various modifications and equivalent arrangements, which fall within the purview of the appended claims.

What is claimed is:

1. A method for extracting DNA, comprising:
   oxidizing carbon nanotubes;
   mixing the oxidized carbon nanotubes into a solution of monohydrated citric acid, thereby synthesizing carbon nanotubes grafted with poly(citric acid);
   admixing the carbon nanotubes grafted with poly(citric acid) with a phenol solution, thereby synthesizing carbon nanotubes grafted with poly(citric acid) encapsulating phenol nanoparticles; and
   applying the carbon nanotubes grafted with poly(citric acid) encapsulating phenol nanoparticles to a sample containing DNA, thereby extracting said DNA.

2. The method according to claim 1, wherein the step of oxidizing the carbon nanotubes comprises mixing the carbon nanotubes, nitric acid, and sulfuric acid to oxidize the carbon nanotubes in a first mixture.

3. The method according to claim 2, wherein the ratio of the nitric acid to the sulfuric acid in the first mixture is about 1 to 3.

4. The method according to claim 1, wherein said carbon nanotubes are selected from the group consisting of single-walled carbon nanotubes, multi-walled carbon nanotubes, and combinations thereof.

5. The method according to claim 1, further comprising:
   extracting the oxidized carbon nanotubes by drying the oxidized carbon nanotubes in a heated environment.

6. The method according to claim 1, wherein the step of mixing comprises dissolving the solution of monohydrated citric acid with oxidized carbon nanotubes in tetrahydrofouran.

7. The method according to claim 1, further comprising:
   extracting, after the step of mixing, the carbon nanotubes grafted with poly(citric acid) by precipitating the solution of monohydrated citric acid with oxidized carbon nanotubes in cyclohexane.

8. A method for synthesizing an extractive agent for DNA extraction and purification, comprising:
   oxidizing carbon nanotubes;
   mixing the oxidized carbon nanotubes into a solution of monohydrated citric acid, thereby synthesizing carbon nanotubes grafted with poly(citric acid); and
   admixing the carbon nanotubes grafted with poly(citric acid) with a phenol solution, thereby synthesizing carbon nanotubes grafted with poly(citric acid) encapsulating phenol nanoparticles, thereby synthesizing said extraction agent.

9. The method according to claim 8, wherein said phenolic compound is selected from the group consisting of phenol, 4-nitrophenol, 4-chloro-3-methylphenol, 2,4-dichlorophenol, and 2,4,6-trinitrophenol (2,4,6-TNP), and mixtures thereof.

10. The method according to claim 8, wherein the step of oxidizing the carbon nanotubes comprises mixing the carbon nanotubes, nitric acid, and sulfuric acid to oxidize the carbon nanotubes in a first mixture.

11. The method according to claim 10, wherein the ratio of the nitric acid to the sulfuric acid in the first mixture is about 1 to 3.

12. The method according to claim 8, wherein said carbon nanotubes are selected from the group consisting of single-walled carbon nanotubes, multi-walled carbon nanotubes, and combinations thereof.

13. The method according to claim 8, further comprising:
    extracting the oxidized carbon nanotubes by drying the oxidized carbon nanotubes in a heated environment.

14. The method according to claim 8, wherein the step of mixing comprises dissolving the solution of monohydrated citric acid with oxidized carbon nanotubes in tetrahydrofouran.

15. The method according to claim 8, further comprising:
    extracting, after the step of mixing, the carbon nanotubes grafted with poly(citric acid) by precipitating the solution of monohydrated citric acid with oxidized carbon nanotubes in cyclohexane.

16. An extractive agent for DNA extraction and purification, comprising:
    a plurality of carbon nanotubes grafted with poly(citric acid),
    wherein phenol nanoparticles are encapsulated in said carbon nanotubes grafted with poly(citric acid).

17. The extractive agent according to claim 16, wherein said carbon nanotubes are selected from the group consisting of single-walled carbon nanotubes, multi-walled carbon nanotubes, and combinations thereof.

18. A method for encapsulating phenolic nanoparticles within carbon nanotubes grafted with poly(citric acid), comprising:
  preparing a solution of a plurality of carbon nanotubes grafted with poly(citric acid); and
  mixing said solution with an aqueous solution of a phenolic compound,
  whereby carbon nanotubes grafted with poly(citric acid) encapsulating phenolic nanoparticles are generated.

19. The method according to of claim 18, wherein said phenolic compound is selected from the group consisting of phenol, 4-nitrophenol, 4-chloro-3-methylphenol, 2,4-dichlorophenol, and 2,4,6-trinitrophenol (2,4,6-TNP), and mixtures thereof.

20. The method according to claim 18, wherein said carbon nanotubes are selected from the group consisting of single-walled carbon nanotubes, multi-walled carbon nanotubes, and combinations thereof.

* * * * *